(12) United States Patent
Flaugh

(10) Patent No.: US 6,180,657 B1
(45) Date of Patent: Jan. 30, 2001

(54) MELATONIN DERIVATIVES FOR USE IN TREATING DESYNCHRONIZATION DISORDERS

(75) Inventor: Michael E. Flaugh, Indianapolis, IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 08/154,903

(22) Filed: Nov. 18, 1993

(51) Int. Cl.⁷ .................. A61K 31/405; A61K 31/40
(52) U.S. Cl. ............................. 514/415; 514/416
(58) Field of Search ..................... 514/415, 416

(56) References Cited

U.S. PATENT DOCUMENTS

| | | |
|---|---|---|
| 4,087,444 | 5/1978 | Flaugh et al. ............ 260/326.13 B |
| 4,600,723 | 7/1986 | Short et al. ................ 514/416 |
| 4,614,807 | 9/1986 | Flaugh ..................... 548/507 |
| 4,665,086 | 5/1987 | Short et al. ................ 514/416 |
| 4,687,763 | 8/1987 | Wurtman .................. 514/53 |
| 4,880,826 | 11/1989 | Zisapel et al. ............. 514/415 |
| 4,997,845 | 3/1991 | Flaugh ..................... 514/415 |
| 5,093,352 | 3/1992 | Dubocovich ............. 514/419 |
| 5,196,435 | 3/1993 | Clemens et al. ........... 514/284 |
| 5,242,941 | 9/1993 | Lewy et al. ............... 514/416 |

FOREIGN PATENT DOCUMENTS

| | | |
|---|---|---|
| 513702 | 11/1992 | (EP) . |
| WO 89/01472 | 2/1989 | (WO) . |

OTHER PUBLICATIONS

Petrie et.al., *Brit. Med. Journal,* 298, 705 (1989).
Arendt et.al., *Brit. Med. Journal,* 292, 1170 (1986).
Armstrong et.al., *Pharm. Biochem & Beh.,* 46, 45 (1993).
Chu et al., *Endocrinology,* 75, 238 (1964).
Blask et al., *J. Neural. Transm.* [Supp.], 21, 433 (1986).
Blask et al., *Neuroindocrinol Lett.,* 9(2), 63 (1987).
Arendt et al., *Ergonomics,* 30, 1379 (1987).
Waldhauser et al., *Psychopharmacology,* 100, 222 (1990).
Guardiola—Lemaitre, *Adv in Pineal Res.,* 5, 351 (1991).
Lieberman et al., *Brain Res.,* 323, 201 (1984).
Nickelsen et al., *J. Pineal Res.,* 6, 325 (1989).
Arendt et al., *Neuroscience Lett.,* 45, 317 (1984).
Wright et al., *Clin. Endocrinology,* 24, 375 (1986).
Frohn et al., (Structure–Activity Relationship of Melatonin Analogues, Life Sciencies, vol. 27, No. 22, pp. 2043–2046 (1980).*

* cited by examiner

*Primary Examiner*—Kevin E. Weddington
(74) *Attorney, Agent, or Firm*—Robert D. Titus

(57) ABSTRACT

The present invention provides a method of treating desynchronization disorders using various melatonin analogs.

21 Claims, No Drawings

MELATONIN DERIVATIVES FOR USE IN TREATING DESYNCHRONIZATION DISORDERS

BACKGROUND OF THE INVENTION

Melatonin, represented by the structure below:

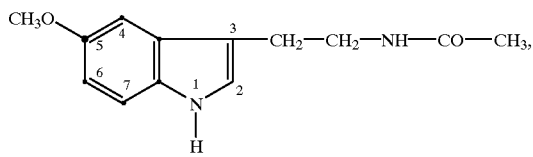

is named systematically as N-[2-(5-methoxy-3-indolyl)ethyl]-acetamide. Trivial names for the compound include N-acetyl-5-methoxytryptamine and N-acetyl-O-methylserotonin. Melatonin is a pineal gland hormone which has ovulation inhibitory activity, Chu et al., *Endocrinology*, 75, 238 (1964), as well as some activity against MCF-7 human breast cancer cells, Blask et al. *J. Neural. Transm.* [Supp.], 21, 433 (1986) and for the treatment of mammalian breast carcinoma, Blask et al., *Neuroendocrinol. Lett.*, 9(2), 63 (1987). Furthermore, melatonin has been known to expedite recovery from "jet lag syndrome", Arendt et al., *Ergonomics*, 30, 1379 (1987), to cause sleep, Waldhauser et al., *Psychopharmacology*, 100, 222 (1990) and to minimize disturbances in circadian rhythms of bodily performance and function, U.S. Pat. Nos. 4,600,723 and 5,242,941.

Several melatonin analogues of the formula

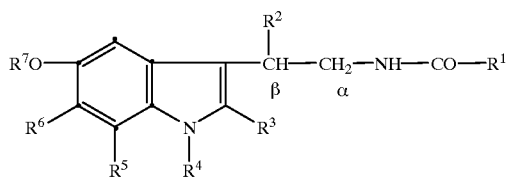

wherein $R^1$ is hydrogen, $C_1$–$C_4$ alkyl or $C_1$–$C_4$ alkoxy;

$R^2$ is hydrogen or $C_1$–$C_4$ alkyl;

$R^3$ is hydrogen or methyl;

$R^4$ is hydrogen, haloacetyl, $C_1$–$C_5$ alkanoyl, benzoyl or benzoyl substituted with halo or methyl;

$R^5$ and $R^6$ are individually hydrogen or halo; and $R^7$ is hydrogen or $C_1$–$C_4$ alkyl;

provided that when $R^2$ is hydrogen, at least one of $R^5$ and $R^6$ is halo, have also been prepared and shown to possess ovulation inhibition activity (see U.S. Pat. Nos. 4,997,845 and 4,614,807). Such analogues are also stated to be active in treating hormonally dependent breast carcinomas in U.S. Pat. No. 5,196,435. However, none of these analogues were previously shown to possess activity in treating desynchronization disorders.

Finally, European Patent Application 513,702 discloses that melatonin and its analogues of the formula

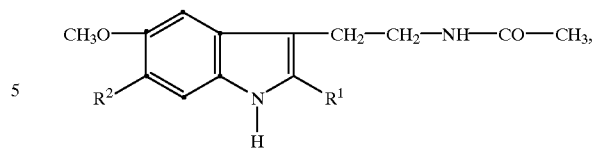

wherein $R^1$ and $R^2$ are the same or different and are hydrogen or halogen can be used in treating sleep disorders and in pre-anesthetic medication. Again, such disclosure does not teach or suggest the use of melatonin analogues for treating desychronization disorders.

It is an object of this invention to provide a method for treating desynchronization disorders by employing certain melatonin analogues. The instant method is believed to provide a more efficacious (in terms of activity, side effect profile and duration of action) means for treating such disorders than previously known. Further, the melatonin analogues used in the instant method are believed to be completely devoid of toxicity at the dosages required for treatment and, as such, a further object of the present invention is to provide a safe, efficacious, method of treating desynchronization disorders. Other objects, features and advantages of the present invention will become apparent from the subsequent description and the appended claims.

SUMMARY OF THE INVENTION

This invention provides a method of treating desynchronization disorders in a mammal suffering from or susceptible to such disorders which comprises administering to said mammal an effective amount of a compound of Formula (I)

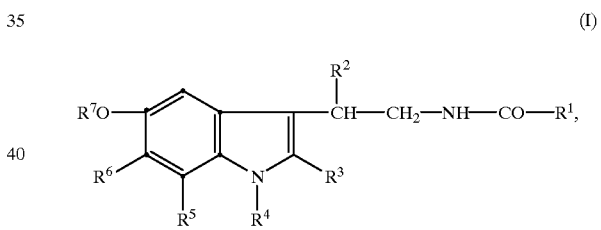

(I)

wherein $R^1$ is hydrogen, $C_1$–$C_4$ alkyl or $C_1$–$C_4$ alkoxy;

$R^2$ is hydrogen or $C_1$–$C_4$ alkyl;

$R^3$ is hydrogen, $C_1$–$C_4$ alkyl, phenyl or substituted phenyl;

$R^4$ is hydrogen, haloacetyl, $C_1$–$C_5$ alkanoyl, benzoyl or benzoyl substituted with halo or methyl;

$R^5$ and $R^6$ are each individually hydrogen or halo; and $R^7$ is hydrogen or $C_1$–$C_4$ alkyl;

provided that when $R^2$ is hydrogen then at least one of $R^5$ and $R^6$ is halo.

DETAILED DESCRIPTION OF THE INVENTION

The following definitions refer to the various terms used above and throughout the disclosure.

The term "halo" refers to fluoro, chloro, bromo and iodo.

The term "$C_1$–$C_4$ alkyl" refers to the straight and branched aliphatic radicals of 1–4 carbon atoms including methyl, ethyl, propyl, isopropyl, n-butyl, isobutyl, sec-butyl and tert-butyl.

The term "$C_1$–$C_4$ alkoxy" includes the straight and branched aliphatic ether radicals of 1–4 carbon atoms such as methoxy, ethoxy, propoxy, isopropoxy, n-butoxy, isobutoxy, sec-butoxy and tert-butoxy.

The term "halocetyl" refers to chloroacetyl, bromoacetyl, fluoroacetyl and iodoacetyl.

The term "$C_1$–$C_5$" alkanoyl" includes formyl, acetyl, propionyl, butyryl, α-methylpropionyl, valeryl, α-methylbutyryl, β-methylbutyryl and pivaloyl.

The term "benzoyl substituted with halo" defines mono- and di-halo benzoyl groups. Specific mono-halo benzoyl groups are chlorobenzoyl, bromobenzoyl, fluorobenzoyl and iodobenzoyl.

Di-halo benzoyl groups include those in which both halo substituents are the same. Typical di-halo benzoyl groups include 2,4-dichlorobenzoyl, 2,4-dibromobenzoyl, 2,4-diflluorobenzoyl and 2,4-diiodobenzoyl.

The term "benzoyl substituted with methyl" contemplates methylbenzoyl, dimethylbenzoyl and trimethylbenzoyl.

The term "substituted phenyl" refers to a phenyl ring which is substituted with one or two substituents selected from the group consisting of halo, $C_1$–$C_4$ alkyl or $C_1$–$C_4$ alkoxy. Examples of such term, therefore, include 4-chlorophenyl, 2-fluorophenyl, 3-iodophenyl, 4-bromophenyl, 3,4-dibromophenyl, 4-methylphenyl, 2-ethylphenyl, 3-n-propylphenyl, 4-isopropyl-phenyl, 4-n-butylphenyl, 3-t-butylphenyl, 4-sec-butylphenyl, 3,4-dimethylphenyl, 4-methoxyphenyl, 3-ethoxyphenyl, 2-n-propylphenyl, 4-isopropoxyphenyl, 3-isobutoxyphenyl, 4-t-butoxyphenyl, 3-ethoxy-4-methoxyphenyl and the like.

While all of the compounds of Formula I are believed to be useful for the method of treating desynchronization disorders presented herein, certain of such compounds are preferred for such use. Preferred compounds of Formula I for use in the instantly claimed method include those compounds wherein $R^1$ is $C_1$–$C_4$ alkyl (especially methyl), $R^3$ is hydrogen or $C_1$–$C_4$ alkyl (especially methyl) and $R^4$ is hydrogen.

Of such preferred compounds, particularly preferred compounds include those wherein $R^2$ and $R^7$ are each independently $C_1$–$C_4$ alkyl (preferably methyl). The most preferred compounds for use in the method of the present invention include N-[2-methyl-2-(5-methoxy-6-fluoroindol-3-yl)ethyl]acetamide, N-[2-ethyl-2-(5-methoxy-6-chloroindol-3-yl)ethyl]acetamide, N-[2-methyl-2-(5-methoxy-6,7-dichloroindol-3-yl)ethyl]acetamide and N-[2-methyl-2-(5-methoxy-6-chloroindol-3-yl)ethyl]acetamide. The later compound is especially preferred for purposes of the present invention.

Those compounds employed in the method of the present invention wherein $R^2$ is $C_1$–$C_4$ alkyl have an asymmetric center at the carbon atom to which such $R^2$ substituent is attached (i.e., the β-carbon atom). As such, such $R^2$ substituted compounds can exist as either a racemic mixture or as individual stereoisomers. All such types of compounds are contemplated for use in the method of the present invention.

The following list illustrates representative compounds suitable for use in the present invention.

N-[2-methyl-2-(5-methoxy-6-chloroindol-3-yl)ethyl]-acetamide
N-[2-methyl-2-(5-methoxy-6-fluoroindol-3-yl)ethyl]-acetamide
N-[2-ethyl-2-(5-methoxy-6-fluoroindol-3-yl)ethyl]-acetamide
N-[2-ethyl-2-(5-methoxy-6-chloroindol-3-yl)ethyl]-acetamide
N-[2-isopropyl-2-(5-methoxy-6-chloroindol-3-yl)ethyl]-acetamide
N-[2-isopropyl-2-(5-methoxy-6-fluoroindol-3-yl)ethyl]-acetamide
N-[2-methyl-2-(5-methoxy-6-bromoindol-3-yl)ethyl]-formamide
N-[2-butyl-2-(5-methoxy-6-bromoindol-3-yl)ethyl]-formamide
N-[2-ethyl-2-(5-propoxy-6-chloroindol-3-yl)ethyl]-formamide
N-[2-propyl-2-(5-isopropoxy-6-iodoindol-3-yl)ethyl]-formamide
N-[2-methyl-2-(5-methoxy-6-chloroindol-3-yl)ethyl]-propionamide
N-[2-ethyl-2-(5-methoxy-6-fluoroindol-3-yl)ethyl]-propionamide
N-[2-methyl-2-(5-ethoxy-6-bromoindol-3-yl)ethyl]-propionamide
N-[2-methyl-2-(5-ethoxy-6-fluoroindol-3-yl)ethyl]-butyramide
N-[2-propyl-2-(5-butoxy-6-chloroindol-3-yl)ethyl]-butyramide
N-[2-methyl-2-(5-methoxy-6-chloroindol-3-yl)ethyl]-butyramide
N-[2-methyl-2-(5-methoxy-7-chloroindol-3-yl)ethyl]-acetamide
N-[2-methyl-2-(5-methoxy-7-fluoroindol-3-yl)ethyl]-acetamide
N-[2-ethyl-2-(5-methoxy-7-chloroindol-3-yl)ethyl]-acetamide
N-[2-propyl-2-(5-methoxy-7-bromoindol-3-yl)ethyl]-acetamide
N-[2-ethyl-2-(5-t-butoxy-7-chloroindol-3-yl)ethyl]-formamide
N-[2-ethyl-2-(5-ethoxy-7-iodoindol-3-yl)ethyl]-formamide
N-[2-methyl-2-(5-isopropoxy-7-chloroindol-3-yl)ethyl]-formamide
N-[2-methyl-2-(5-methoxy-7-bromoindol-3-yl)ethyl]-propionamide
N-[2-ethyl-2-(5-propoxy-7-chloroindol-3-yl)ethyl]-propionamide
N-[2-methyl-2-(5-s-butoxy-7-fluoroindol-3-yl)ethyl]-propionamide
N-[2-methyl-2-(5-methoxy-7-chloroindol-3-yl)ethyl]-butyramide
N-[2-butyl-2-(5-ethoxy-7-chloroindol-3-yl)ethyl]-butyramide
N-[2-ethyl-2-(5-methoxy-7-fluoroindol-3-yl)ethyl]-butyramide
N-[2-methyl-2-(5-methoxy-6,7-dichloroindol-3-yl)ethyl]acetamide
N-[2-ethyl-2-(5-methoxy-6,7-dichloroindol-3-yl)ethyl]acetamide
N-[2-isopropyl-2-(5-methoxy-6,7-dichloroindol-3-yl)ethyl]acetamide
N-[2-methyl-2-(5-isopropoxy-6,7-dichloroindol-3-yl)ethyl]acetamide
N-[2-methyl-2-(5-methoxy-6,7-difluoroindol-3-yl)ethyl]acetamide
N-[2-propyl-2-(5-methoxy-6,7-difluoroindol-3-yl)ethyl]acetamide
N-[2-ethyl-2-(5-butoxy-6,7-difluoroindol-3-yl)ethyl]acetamide
N-[2-methyl-2-(5-methoxy-6-chloro-7-fluoroindol-3-yl)ethyl]acetamide
N-[2-methyl-2-(5-methoxy-6-chloro-7-bromoindol-3-yl)ethyl]acetamide N-[2-methyl-2-(5-methoxy-6-fluoro-7-chloroindol-3-yl)ethyl]acetamide
N-[2-methyl-2-(5-ethoxy-6-bromo-7-iodoindol-3-yl)ethyl]acetamide
N-[2-ethyl-2-(5-ethoxy-6-chloro-7-fluoroindol-3-yl)ethyl]acetamide
N-[2-isopropyl-2-(5-t-butoxy-6-chloro-7-fluoro-indol-3-yl)ethyl]acetamide
N-[2-ethyl-2-(5-butoxy-6-bromo-7-chloroindol-3-yl)ethyl]acetamide
N-[2-methyl-2-(5-methoxy-6,7-dichloroindol-3-yl)ethyl]formamide
N-[2-methyl-2-(5-methoxy-6,7-dibromoindol-3-yl)ethyl]formamide
N-[2-t-butyl-2-(5-methoxy-6-chloro-7-fluoroindol-3-yl)ethyl]formamide
N-[2-ethyl-2-(5-ethoxy-6-fluoro-7-bromoindol-3-yl)ethyl]formamide
N-[2-ethyl-2-(5-s-butoxy-6-fluoro-7-chloroindol-3-yl)ethyl]formamide
N-[2-methyl-2-(5-methoxy-6,7-dichloroindol-3-yl)ethyl]propionamide
N-[2-ethyl-2-(5-methoxy-6,7-dichloroindol-3-yl)ethyl]propionamide
N-[2-propyl-2-(5-isopropoxy-6-chloro-7-fluoroindol-3-yl)ethyl]propionamide
N-[2-methyl-2-(5-methoxy-6-bromo-7-iodoindol-3-yl)ethyl]propionamide
N-[2-methyl-2-(5-ethoxy-6-bromo-7-chloroindol-3-yl)ethyl]propionamide
N-[2-methyl-2-(5-methoxy-6,7-difluoroindol-3-yl)ethyl]butyramide
N-[2-ethyl-2-(5-methoxy-6-fluoro-7-chloroindol-3-yl)ethyl]butyramide
N-[2-isopropyl-2-(5-methoxy-6,7-dibromoindol-3-yl)ethyl]butyramide
N-[2-isopropyl-2-(5-butoxy-6-bromo-7-chloroindol-3-yl)ethyl]butyramide
N-[2-ethyl-2-(5-methoxy-6,7-dichloro-3-yl)ethyl]butyramide
N-[2-methyl-2-(1-acetyl-5-methoxy-6-chloroindol-3-yl)ethyl]acetamide
N-[2-butyl-2-(1-acetyl-5-methoxy-6-fluoroindol-3-yl)ethyl]acetamide
N-[2-ethyl-2-(1-acetyl-5-isopropoxy-6-chloro-7-fluoroindol-3-yl)ethyl]acetamide
N-[2-methyl-2-(1-propionyl-5-methoxy-6-fluoroindol-3-yl)ethyl]acetamide
N-[2-methyl-2-(1-propionyl-5-ethoxy-6,7-dichloroindol-3-yl)ethyl]acetamide
N-[2-ethyl-2-(1-propionyl-5-butoxy-7-chloroindol-3-yl)ethyl]acetamide
N-[2-methyl-2-(1-pivaloyl-5-ethoxy-6-bromoindol-3-yl)ethyl]formamide
N-[2-propyl-2-(1-chloroacetyl-5-methoxy-6-bromo-7-fluoroindol-3-yl)ethyl]propionamide
N-[2-methyl-2-(1-bromoacetyl-5-ethoxy-7-chloro-indol-3-yl)ethyl]butyramide
N-[2-ethyl-2-(1-valeryl-5-isopropoxy-6,7-dichloroindol-3-yl)ethyl]acetamide
N-[2-methyl-2-(1-butyryl-5-methoxy-6-chloroindol-3-yl)ethyl]acetamide
N-[2-ethyl-2-(1-benzoyl-5-t-butoxy-7-bromoindol-3-yl)ethyl]formamide
N-[[2-isopropyl-2-[1-(4-chlorobenzoyl)-5-methoxy-7-fluoroindol-3-yl]ethyl]]formamide
N-[[2-methyl-2-[1-(4-bromobenzoyl)-5-ethoxy-6,7-dichloroindol-3-yl]ethyl]]propionamide
N-[[2-ethyl-2-[1-(2,4-dichlorobenzoyl)-5-methoxy-7-bromoindol-3-yl]ethyl]]propionamide
N-[[2-methyl-2-[1-(2,4-difluorobenzoyl)-5-propoxy-6-chloroindol-3-yl]ethyl]]formamide
N-[[2-methyl-2-[1-(4-iodobenzoyl)-5-ethoxy-6-fluoro-7-chloroindol-3-yl]ethyl]]acetamide
N-[[2-ethyl-2-[1-(2-methylbenzoyl)-5-methoxyindol-3-yl]ethyl]]propionamide
N-[[2-methyl-2-[1-(4-fluorobenzoyl)-5-ethoxyindol-3-yl]ethyl]]formamide
N-[[2-methyl-2-[1-(2,6-dimethylbenzoyl)-5-methoxy-7-fluoroindol-3-yl]ethyl]]formamide
N-[[2-ethyl-2-[1-(2,6-dimethylbenzoyl)-5-ethoxyindol-3-yl]ethyl]]acetamide
N-[[2-ethyl-2-[1-(2,4,6-trimethoxybenzoyl)-5-methoxy-6-chloroindol-3-yl]ethyl]]propionamide
N-[[2-methyl-2-[1-(2,4,6-trimethoxybenzoyl)-5-methoxyindol-3-yl]ethyl]]formamide
N-[2-ethyl-2-(1-pivaloyl-5-isopropoxyindol-3-yl)ethyl]acetamide
N-[2-methyl-2-(1-chloroacetyl-5-methoxyindol-3-yl)ethyl]butyramide
N-[2-methyl-2-(5-methoxyindol-3-yl)ethyl]acetamide
N-[2-ethyl-2-(5-methoxyindol-3-yl)ethyl]acetamide
N-[2-ethyl-2-(5-methoxyindol-3-yl)ethyl]propionamide
N-[2-methyl-2-(5-propoxyindol-3-yl)ethyl]formamide
N-[2-methyl-2-(5-s-butoxyindol-3-yl)ethyl]butyramide
N-[2-ethyl-2-(5-ethoxyindol-3-yl)ethyl]propionamide
N-[2-methyl-2-(5-ethoxyindol-3-yl)ethyl]formamide
N-[2-isopropyl-2-(5-methoxyindol-3-yl)ethyl]acetamide
N-[2-ethyl-2-(5-methoxyindol-3-yl)ethyl]formamide
N-[2-(5-methoxy-6-chloroindol-3-yl)ethyl]acetamide
N-[2-(5-methoxy-6-fluoroindol-3-yl)ethyl]acetamide
N-[2-(5-methoxy-6-bromoindol-3-yl)ethyl]formamide
N-[2-(5-methoxy-6-iodoindol-3-yl)ethyl]propionamide
N-[2-(5-methoxy-6-chloroindol-3-yl)ethyl]-n-butyramide
N-[2-(2-methyl-5-methoxy-6-bromoindol-3-yl)ethyl]-acetamide
N-[2-(2-ethyl-5-methoxy-6-chloroindol-3-yl)ethyl]-acetamide
N-[2-(2-n-propyl-5-methoxy-6-chloroindol-3-yl)ethyl]-formamide
N-[2-(2-n-butyl-5-methoxy-6-chloroindol-3-yl)ethyl]-formamide
N-[2-(2-ethyl-5-methoxy-6-iodoindol-3-yl)ethyl]-propionamide
N-[2-(2-isopropyl-5-methoxy-6-fluoroindol-3-yl)ethyl]α-methylpropionamide
N-[2-(2-phenyl-5-methoxy-6-chloroindol-3-yl)ethyl]-formamide
N-[2-(2-phenyl-5-methoxy-6-bromoindol-3-yl)ethyl]-acetamide
N-[2-(2-phenyl-5-methoxy-6-iodoindol-3-yl)ethyl]-propionamide
N-[2-((2-(4-chlorophenyl)-5-methoxy-6-chloroindol-3-yl))ethyl]formamide
N-[2-((2-(3-fluorophenyl)-5-methoxy-6-bromoindol-3-yl))ethyl]acetamide
N-[2-((2-(2-fluorophenyl)-5-methoxy-6-chloroindol-3-yl))ethyl]propionamide
N-[2-((2-(4-methylphenyl)-5-methoxy-6-bromoindol-3-yl))ethyl]formamide
N-[2-((2-(3-ethylphenyl)-5-methoxy-6-fluoroindol-3-yl))ethyl]butyramide
N-[2-((2-(4-n-propylphenyl)-5-methoxy-6-chloroindol-3-yl))ethyl]formamide
N-[2-((2-(3-isopropylphenyl)-5-methoxy-6-fluoroindol-3-yl))ethyl]acetamide N-[2-((2-(4-methoxyphenyl)-5-methoxy-6-chloroindol-3-yl))ethyl]propionamide
N-[2-((2-(3-ethoxyphenyl)-5-methoxy-6-bromoindol-3-yl))ethyl]acetamide
N-[2-((2-(3-n-propoxyphenyl)-5-methoxy-6-fluoroindol-3-yl))ethyl]acetamide
N-[2-((2-(4-t-butoxyphenyl)-5-methoxy-6-chloroindol-3-yl))ethyl]formamide
N-[2-((2-(3-n-butoxyphenyl)-5-methoxy-6-chloroindol-3-yl))ethyl]acetamide
N-[2-(1-acetyl-5-methoxy-6-chloroindol-3-yl)ethyl]acetamide
N-[2-(1-propionyl-5-methoxy-6-fluoroindol-3-yl)ethyl]acetamide
N-[2-(1-pivaloyl-5-methoxy-6-bromoindol-3-yl)ethyl]formamide
N-[2-(1-chloroacetyl-5-methoxy-6-iodoindol-3-yl)ethyl]propionamide
N-[2-(1-bromoacetyl-5-methoxy-6-chloroindol-3-yl)ethyl]-n-butyramide
N-[2-(1-valeryl-2-methyl-5-methoxy-6-bromoindol-3-yl)ethyl]acetamide
N-[2-(1-butyryl-2-ethyl-5-methoxy-6-chloroindol-3-yl)ethyl]acetamide
N-[2-(1-benzoyl-2-n-propyl-5-methoxy-6-chloroindol-3-yl)ethyl]formamide
N-[[2-[1-(4-chlorobenzoyl)-2-n-butyl-5-methoxy-6-chloroindol-3-yl]ethyl]]formamide
N-[[2-[-(4-bromobenzoyl)-2-ethyl-5-methoxy-6-iodoindol-3-yl]ethyl]]propionamide
N-[[2-[1-(2,4-dichlorobenzoyl)-2-isopropyl-5-methoxy-6-fluoroindol-3-yl]ethyl]]-α-methylpropionamide
N-[[2-[1-(2,4-difluorobenzoyl)-2-phenyl-5-methoxy-6-chloroindol-3-yl]ethyl]]formamide
N-[[2-[1-(4-iodobenzoyl)-2-phenyl-5-methoxy-6-bromoindol-3-yl]ethyl]]acetamide
N-[[2-[1-(2-methylbenzoyl)-2-phenyl-5-methoxy-6-iodoindol-3-yl]ethyl]]propionamide
N-[[2-[1-(2,6-dimethylbenzoyl)-2-(4-chloro-phenyl)-5-methoxy-6-chloroindol-3-yl]ethyl]]formamide
N-[[2-[1-(2,4,6-trimethylbenzoyl)-2-(3-fluoro-phenyl)-5-methoxy-6-bromoindol-3-yl]ethyl]]acetamide
N-[2-(1-pivaloyl-5-methoxy-6-chloroindol-3-yl)ethyl]acetamide
N-[2-(1-chloroacetyl-5-methoxy-6-chloroindol-3-yl)ethyl]acetamide
N-[[2-[1-(4-chlorobenzoyl)-5-methoxy-6-chloroindol-3-yl]ethyl]]acetamide
N-[[2-[1-(2,4-dichlorobenzoyl)-5-methoxy-6-chloroindol-3-yl]ethyl]]acetamide
N-[[2-[1-(2-methylbenzoyl)-5-methoxy-6-chloroindol-3-yl]ethyl]]acetamide
N-[[2-[1-(2,6-dimethylbenzoyl)-5-methoxy-6-chloroindol-3-yl]ethyl]]acetamide
N-[[2-[1-(2,4,6-trimethylbenzoyl)-5-methoxy-6-chloroindol-3-yl]ethyl]]acetamide
N-[2-(5-methoxy-6,7-dichloroindol-3-yl)ethyl]acetamide
N-[2-(2-methyl-5-methoxy-6,7-difluoroindol-3-yl)ethyl]acetamide
N-[2-(2-methyl-5-methoxy-6-fluoro-7-chloroindol-3-yl)ethyl]acetamide
N-[2-(5-methoxy-6,7-dichloroindol-3-yl)ethyl]propionamide
N-[2-(5-methoxy-6,7-difluoroindol-3-yl)ethyl]isobutyramide
N-[2-(2-methyl-5-methoxy-6,7-dichloroindol-3-yl)ethyl]-n-butyramide; and the like.

The compounds employed in the method of this invention are known in the art or can be made by methods described in the art. Representative publications which teach the preparation of compounds of Formula I include U.S. Pat. Nos. 4,087,444; 4,614,807; and 4,997,845. The teaching of all such patents is hereby incorporated by reference.

The compounds of Formula I, as used in this invention, are useful in treating desynchronization disorders in mammals. Such disorders result when a mammal's normal circadian rhythms of sleep latency, alertness, food and drink appetite, body temperature, cardiovascular activity, urinary urge, electrolyte excretion or mitotic activity are not synchronized to the local day/night pattern. Such desynchronization, which can result not only from travel but from changes in daily routine such as changes caused by a time shift due to daylight savings time or a workshift change (from days to nights, etc.) or from inadequate or inappropriate exposure to daylight or particularly bright artificial light, is often termed "jet lag". A discussion of desynchronized circadian rhythms, and the causes of same, is provided in U.S. Pat. Nos. 4,600,723 and 5,242,941. The teachings of such patents with respect to the scope, extent and cause of desynchronization disorders is herein incorporated by reference.

As discussed above, the compounds of Formula I are useful in treating circadian rhythm desynchronization disorders in mammals. Such method comprises administering to a mammal (preferably a human) in need of such treatment a sufficient amount of one or more compounds of Formula I so as to achieve the therapeutic or prophylactic intervention desired. The compounds can be administered by a variety of routes including the oral, rectal, transdermal, subcutaneous, intravenous, intramuscular or intranasal routes. The oral and transdermal routes are preferred. No matter what route of administration is chosen, such administration is accomplished by means of pharmaceutical compositions which are prepared by techniques well known in the pharmaceutical sciences.

The method of the present invention encompasses creating desynchronization disorders in a prophylactic manner (i.e., using the compounds of Formula I to treat a desynchronization disorder in a mammal susceptible to such condition before the condition actually occurs). Such prophylactic method of administration may be especially appropriate in those instances where the patient is about to go on a trans-meridian flight or is about to change from a day shift job to a night shift job or vice versa.

The method of treating desynchronization disorders provided by the present invention entails phase shifting of circadian rhythms by administration of a compound of Formula I. The method described in this invention can be used to advance or delay the phase of circadian rhythms in mammals. Phase-advance of the circadian rhythms is accomplished by administering a compound of Formula I to a patient anywhere from the time when the patient's normal sleep phase should begin up to about 10 hours prior to that time (preferably 3 to 8 hours). Phase-advance of circadian rhythms is particularly useful for alleviating jet lag caused by west to east travel and for improving bodily performance and function when transferring from a day to a night shift.

Phase-delay of the circadian rhythms, on the other hand, is accomplished by administering a compound of Formula I to a patient about 11 hours to about 19 hours prior to commencement of a patient's normal sleep phase. Phase-delay of circadian rhythms is particularly useful for alleviating jet lag caused by east to west travel and for improving bodily performance and function when transferring from a night to day shift.

As mentioned above, the method of the present invention utilizes pharmaceutical compositions. In making these compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 0.1 to about 25 mg, more usually about 0.5 to about 5 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds employed in the method of the present invention are effective over a dosage range of about 0.1 mg/day to about 25 mg/day for treating desynchronization disorders. Thus, as used herein, the term "effective amount" refers to a dosage range of from about 0.1 to about 25 mg of active ingredient per day. In the treatment of adult humans, the range of about 0.1 to about 5 mg of active ingredient per day, in single or divided doses, is preferred.

In some patients, the amount of compound of Formula I required to obtain resynchronization of circadian rhythms may be greater than 25 mg/day. In these patients, who are mostly elderly in nature, the pineal gland is no longer capable of secreting its principal hormone, melatonin. Such loss of melatonin secretion affects the patient's normal circadian rhythm pattern thus causing "non-functional desynchronization". To resynchronize such patients, one must supply the patient with a sufficient amount of a compound of Formula I so as to offset the patient's loss of secreted melatonin. In many instances this amount will be greater than 25 mg/day since, while the amount of melatonin needed to obtain a normal circadian rhythm pattern is usually quite low, the amount of melatonin needed to obtain resynchronization of a "non-functional desynchronized" patient needs to be high enough to provide a sustained level of melatonin in the body for several hours. The present invention encompasses treatment of both non-functional desynchronization disorders as well as normal desynchronization disorders (i.e., those wherein resynchronization is obtained by using small doses of a compound of Formula I in conjunction with the patient's own secreted melatonin).

The following formulation examples may employ as active ingredient any of the compounds of Formula I. The examples are illustrative only and are not intended to limit the scope of the invention in any way.

EXAMPLE 1

Hard gelatin capsules suitable for treating a desynchronization disorder are prepared using the following ingredients:

|  | Quantity (mg/capsule) |
| --- | --- |
| (±)-N-[2-methyl-2-(5-methoxy)-6-chloroindol-3-yl)ethyl]acetamide | 10 |
| Starch dried | 200 |
| Magnesium stearate | 10 |

The above ingredients are mixed and filled into hard gelatin capsules in 220 mg quantities.

EXAMPLE 2

A tablet suitable for treating desynchronization disorders is prepared using the ingredients below:

|  | Quantity (mg/tablet) |
| --- | --- |
| (−)-N-[2-methyl-2-(5-methoxy)-6-chloroindol-3-yl)ethyl]acetamide | 5 |
| Cellulose, microcrystalline | 400 |
| Silicon dioxide | 10 |
| Stearic acid | 5 |

The components are blended and compressed to form tablets each weighing 420 mg.

EXAMPLE 3

An aerosol solution suitable for treating desynchronization disorders is prepared containing the following components:

|  | Weight |
| --- | --- |
| (±)-N-[2-methyl-2-(5-methoxy)-6-fluoroindol-3-yl)ethyl]acetamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. Valve units are then fitted to the container.

EXAMPLE 4

Tablets suitable for treating a desynchronization disorder, each containing 1 mg of active ingredient are made up as follows:

| | |
|---|---|
| (+)-N-[2-methyl-2-(5-methoxy)-6-chloroindol-3-yl)ethyl]acetamide | 1 mg |
| Starch | 44 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 90 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 90 mg.

EXAMPLE 5

Capsules suitable for treating desynchronization disorders, each containing 10 mg of medicament, are made as follows:

| | |
|---|---|
| (−)-N-[2-methyl-2-(5-methoxy)-6,7-dichloroindol-3-yl)ethyl]acetamide | 10 mg |
| Starch | 59 mg |
| Microcrystalline cellulose | 59 mg |
| Magnesium stearate | 2 mg |
| Total | 130 mg |

The active ingredient, cellulose, starch and magnesium stearate are blended, passed through a No. 45 mesh U.S. sieve, and filled into hard gelatin capsules in 130 mg quantities.

EXAMPLE 6

Suppositories suitable for treating desynchronization disorders, each containing 20 mg of active ingredient, are made as follows:

| | |
|---|---|
| (±)-N-[2-ethyl-2-(5-methoxy)-6-chloroindol-3-yl)ethyl]acetamide | 20 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions suitable for treating desynchronization disorders, each containing 5 mg of medicament per 5 ml dose, are made as follows:

| | |
|---|---|
| (±)-N-[2-methyl-2-(5-methoxy-6-chloroindol-3-yl)ethyl]acetamide | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules suitable for use in treating a desynchronization disorder, each containing 15 mg of medicament, are made as follows:

| | |
|---|---|
| (±)-N-[2-methyl-2-(5-methoxy)-6,7-dichloroindol-3-yl)ethyl]acetamide | 15 mg |
| Starch | 164 mg |
| Microcrystalline cellulose | 164 mg |
| Magnesium stearate | 22 mg |
| Total | 365 mg |

The active ingredient, cellulose, starch and magnesium stearate are blended, passed through a No. 45 mesh U.S. sieve, and filled into hard gelatin capsules in 365 mg quantities.

I claim:

1. A method of treating desynchronization disorders in a mammal suffering from or susceptible to such disorders which comprises administering to said mammal an effective amount of a compound of the formula

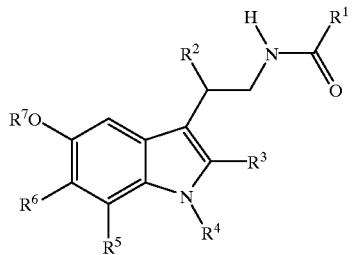

wherein
  $R^1$ is hydrogen, $C_1$–$C_4$ alkyl or $C_1$–$C_4$ alkoxy;
  $R^2$ is $C_1$–$C_4$ alkyl;
  $R^3$ is hydrogen, $C_1$–$C_4$ alkyl, phenyl, or substituted phenyl;
  $R^4$ is hydrogen, haloacetyl, $C_1$–$C_5$ alkanoyl, benzoyl or benzoyl substituted with halo or methyl;
  $R^5$ and $R^6$ are each independently hydrogen or halo; and
  $R^7$ is hydrogen or $C_1$–$C_4$ alkyl.

2. A method of claim 1 which employs a compound wherein $R^4$ is hydrogen.

3. A method of claim 2 which employs a compound wherein $R^1$ is $C_1$–$C_4$ alkyl.

4. A method of claim 3 which employs a compound wherein $R^3$ is hydrogen or $C_1$–$C_4$ alkyl.

5. A method of claim 4 which employs a compound wherein $R^1$ is methyl and $R^3$ is hydrogen.

6. A method of claim 4 which employs a compound wherein both $R^1$ and $R^3$ are methyl.

7. A method of claim 4 which employs a compound wherein $R^7$ is $C_1$–$C_4$ alkyl.

8. A method of claim 7 which employs a compound wherein $R^7$ is methyl.

9. A method of claim 8 which employs a compound wherein $R^2$ is methyl.

10. A method of claim 9 which employs N-[2-methyl-2-(5-methoxy-6-fluoroindol-3-yl)ethyl]acetamide.

11. A method of claim 8 which employs N-[2-ethyl-2-(5-methoxy-6-chloroindol-3-yl)ethyl]acetamide.

12. A method of claim 9 which employs N-[2-methyl-2-(5-methoxy-6,7-dichloroindol-3-yl)ethyl]acetamide.

13. A method of claim 9 which employs N-[2-methyl-2-(5-methoxy-6-chloroindol-3-yl)ethyl]acetamide.

14. A method of claim 13 which employs the racemate of the compound described therein.

15. A method of claim 13 which employs the (−) stereoisomer of the compound described therein.

16. A method of claim 13 which employs the (+) stereoisomer of the compound described therein.

17. The method of claim 1 wherein the treatment of desynchronization disorders entails a phase-advance of a mammal's circadian rhythms.

18. The method of claim 17 wherein said phase-advance is accomplished by administering a compound of such method to said mammal anywhere from the time when the mammal's normal sleep phase should begin up to about ten hours prior to that time.

19. The method of claim 18 wherein said phase-advance is accomplished by administering a compound of such method to said mammal anywhere from three hours to eight hours prior to the time when the mammals normal sleep phase should begin.

20. The method of claim 1 wherein the treatment of desynchronization disorders entails a phase-delay of a mammal's circadian rhythms.

21. The method of claim 20 wherein said phase-delay is accomplished by administering a compound of such method to said mammal about eleven hours to about 19 hours prior to the time when the mammal's normal sleep phase should begin.

* * * * *